US008975440B2

(12) United States Patent
May et al.

(10) Patent No.: US 8,975,440 B2
(45) Date of Patent: Mar. 10, 2015

(54) METHOD FOR PRODUCING A CARBOXYLIC ACID AMIDE FROM A CARBONYL COMPOUND AND HYDROCYANIC ACID

(75) Inventors: Alexander May, Seeheim-Jugenheim (DE); Martin Koestner, Darmstadt (DE); Joerg Becker, Darmstadt (DE); Joerg Schallenberg, Karlstein (DE); Hermann Siegert, Seeheim-Jugenheim (DE); Bernd Vogel, Wiesbaden (DE)

(73) Assignee: Evonik Roehm GmbH, Darmstadt (DE)

( * ) Notice: Subject to any disclaimer, the term of this patent is extended or adjusted under 35 U.S.C. 154(b) by 952 days.

(21) Appl. No.: 13/131,462

(22) PCT Filed: Oct. 29, 2009

(86) PCT No.: PCT/EP2009/064279
§ 371 (c)(1),
(2), (4) Date: Aug. 4, 2011

(87) PCT Pub. No.: WO2010/063520
PCT Pub. Date: Jun. 10, 2010

(65) Prior Publication Data
US 2011/0306784 A1    Dec. 15, 2011
US 2012/0232305 A2    Sep. 13, 2012

(30) Foreign Application Priority Data

Dec. 1, 2008 (DE) .......................... 10 2008 044 218

(51) Int. Cl.
| C07C 231/06 | (2006.01) |
| C07C 253/30 | (2006.01) |
| C07C 67/327 | (2006.01) |
| C07C 253/06 | (2006.01) |
| C07C 255/13 | (2006.01) |
| C07C 69/54 | (2006.01) |
| C07C 231/14 | (2006.01) |
| C07C 253/00 | (2006.01) |

(52) U.S. Cl.
CPC ........... *C07C 231/06* (2013.01); *C07C 231/065* (2013.01); *C07C 231/14* (2013.01); *C07C 253/00* (2013.01)
USPC .......................................... 564/125; 564/126

(58) Field of Classification Search
None
See application file for complete search history.

(56) References Cited

U.S. PATENT DOCUMENTS

| 4,018,829 | A  | 4/1977 | Gruber et al. |
| 5,087,736 | A  | 2/1992 | Higuchi et al. |
| 6,372,846 | B1 | 4/2002 | McGrail et al. |
| 7,928,251 | B2 | 4/2011 | Vogel et al. |
| 2008/0194862 | A1 | 8/2008 | Ackermann et al. |
| 2009/0182167 | A1 | 7/2009 | May et al. |
| 2010/0021977 | A1 | 1/2010 | May et al. |
| 2010/0029979 | A1 | 2/2010 | Vogel et al. |
| 2011/0034728 | A1 | 2/2011 | May et al. |
| 2011/0060159 | A1 | 3/2011 | May et al. |

FOREIGN PATENT DOCUMENTS

| DE | 2 202 660 | 7/1973 |
| DE | 10 2006 055 426 A1 | 5/2008 |
| DE | 10 2006 055 427 A1 | 5/2008 |
| DE | 10 2006 055 430 | 5/2008 |
| DE | 10 2007 011 706 A1 | 9/2008 |
| EP | 0 407 811 | 1/1991 |
| EP | 0407811 A2 | 1/1991 |
| JP | 3-48638 A | 3/1991 |
| JP | 6-172283 A | 6/1994 |
| JP | H06-172283 | 6/1994 |
| JP | 2002-371046 A | 12/2002 |
| JP | 2010-510276 A | 4/2010 |
| TW | 477805 | 3/2002 |
| WO | WO 2008/061822 A1 | 5/2008 |

OTHER PUBLICATIONS

Office Action issued Sep. 19, 2013 in European Patent Application No. 09751855.9.
"Ullmann's Encyclopedia of Industrial Chemistry," vol. A1, VCH 1985, pp. 91 to 92.
International Search Report issued May 7, 2010 in PCT/EP09/64279 filed Oct. 29, 2009.
Combined Taiwanese Office Action and Search Report issued Apr. 3, 2014 in Patent Application No. 098140350 with English Translation of Categories of Cited Documents.
European Search Report issued Mar. 6, 2013, in European Patent Application No. 09 751855.9.
Third Party Observations issued Jan. 25, 2013, in European Patent Application No. 09 751855.9.
German Search Report issued Jul. 27, 2009, in German Patent Application No. 10 2008 044 218.6 with English translation of category of cited documents.

(Continued)

*Primary Examiner* — Yevegeny Valenrod
(74) *Attorney, Agent, or Firm* — Oblon, McClelland, Maier & Neustadt, L.L.P.

(57) ABSTRACT

The invention relates to a method for producing a carboxylic acid amide from a carbonyl compound and hydrocyanic acid, comprising the steps of A) reacting a carbonyl compound with hydrocyanic acid to produce a hydroxycarboxylic acid nitrile, B) hydrolysis of the hydroxycarboxylic acid nitrile obtained in step A) in the presence of a catalyst comprising manganese dioxide, wherein a molar excess of carbonyl compound is used in relation to the hydrocyanic acid to react the carbonyl compound with hydrocyanic acid according to step A), and the reaction mixture obtained in step A) is not purified by distillation before the hydrolysis according to step B) is carried out. The invention furthermore relates to a method for producing alkyl(meth)acrylates from polymers, moulding compounds and moulded bodies, wherein a method for producing a carboxylic acid amide from a carbonyl compound and hydrocyanic acid is carried out in accordance with the method described above.

17 Claims, 1 Drawing Sheet

(56) References Cited

OTHER PUBLICATIONS

Transmittal of third party Observations issued May 20, 2013, in Japanese Patent Application No. 2011-538919 (submitting German translation only).

English translation of the Office Action issued Nov. 25, 2013 in Japanese Patent Application No. 2011-538919.

Communication pursuant to Article 94(3) EPC issued Nov. 22, 2013 in European Patent Application No. 09 751 855.9 (with English language translation).

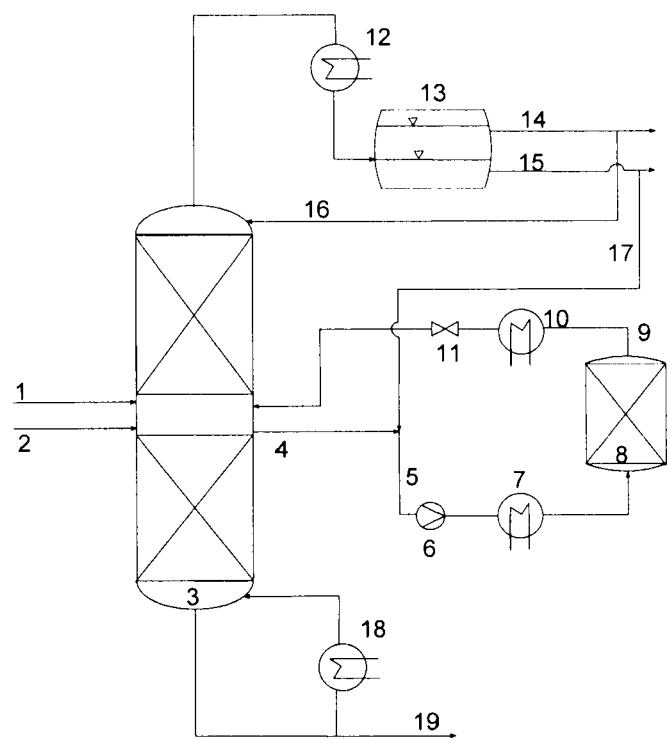

METHOD FOR PRODUCING A CARBOXYLIC ACID AMIDE FROM A CARBONYL COMPOUND AND HYDROCYANIC ACID

BACKGROUND OF THE INVENTION

1. Field of the Invention

The present invention relates to a process for preparing a carboxamide from a carbonyl compound and hydrogen cyanide. The present invention further relates to a process for preparing alkyl (meth)acrylates and polymers, and for producing moulding materials and polymer mouldings.

2. Description of the Background

The preparation of carboxamides by the hydrolysis of carbonitriles in the presence of a catalyst comprising manganese dioxide has been prior art for some time. Carboxamides are required as an intermediate in many cases in industry. For example, α-hydroxyisobutyramide can serve to prepare methacrylic acid or methacrylic esters, especially methyl methacrylate.

A particularly preferred process for preparing carboxamides is detailed in WO 2008/061822 A1.

Even though the teaching of the document detailed above already leads to a relatively inexpensive preparation, there is a permanent need to further improve the process. Typically, the cyanohydrin obtained by reaction of hydrogen cyanide and carbonyl compound, especially acetone, is stabilized by addition of acid. This stabilization has to be removed before the conversion of the cyanohydrin to the carboxamide, which is typically done by distillation. WO 2008/061822 A1 states that the mixture obtained after the reaction of acetone with hydrogen cyanide can be used for hydrolysis. However, it is not stated whether a purification has to be effected. In general, this purification comprises a two-stage distillation, the unconverted reactants being removed in a first stage. In a second stage, the acid used for stabilization is typically removed from the cyanohydrin. If no purification is performed, for example by distillation, relatively short catalyst service lives are obtained. In the case of use of a distilled reaction mixture, the service life of the catalyst can be improved considerably, although the overall efficiency of the process is worsened as a result owing to the energy consumption by the distillation.

In view of the prior art, it is thus an object of the present invention to provide processes for preparing carboxamides, which can be performed in a particularly simple and inexpensive manner and with a high yield. More particularly, a particular problem was to provide a process which, with a high rate, low energy use and low yield losses, ensures a particularly long lifetime of the catalyst and a long service life of the plant for preparing the carboxamide.

These objects and further objects which are not stated explicitly but are immediately derivable or discernible from the connections discussed herein by way of introduction are achieved by a process having all features of Claim 1. Appropriate modifications of the process according to the invention are protected in dependent claims. With regard to the process for preparing alkyl (meth)acrylates and polymers and for producing moulding materials and polymer mouldings, Claims 22, 24, 26 and 27 provide solutions to the problems underlying these objects.

BRIEF DESCRIPTION OF THE DRAWING

FIG. 1 schematically shows a still according to a preferred embodiment of the invention.

SUMMARY OF THE INVENTION

Accordingly, the present invention provides a process for preparing a carboxamide from a carbonyl compound and hydrogen cyanide, comprising the steps of
A) reacting a carbonyl compound with hydrogen cyanide to prepare a hydroxycarbonitrile,
B) hydrolysing the hydroxycarbonitrile obtained in step A) in the presence of a catalyst comprising manganese dioxide, which is characterized in that a molar excess of carbonyl compound in relation to the hydrogen cyanide is used for the reaction of the carbonyl compound with hydrogen cyanide in step A), and the reaction mixture obtained in step A) is not purified by distillation before the hydrolysis in step B) is performed. It is thus surprisingly possible to provide a particularly energy-efficient process which enables long catalyst service lives.

DETAILED DESCRIPTION OF THE INVENTION

At the same time, the processes according to the invention can achieve a series of further advantages. One of these is that the process according to the invention can prolong the service life of the plant for preparing the carboxamide to a surprisingly significant degree. This allows the process to be performed particularly efficiently, inexpensively, at high rate, and with low energy use and low yield losses.

The process according to the invention enables the efficient preparation of carboxamides. In this process, especially carbonyl compounds are used, which generally have groups of the formula —CO—. Carboxamides comprise at least one group of the formula —CONH$_2$. These compounds are known in the technical field and are described, for example, in Römpp Chemie Lexikon 2nd Edition on CD-ROM.

The reactants used may especially be aliphatic or cycloaliphatic carbonyl compounds, saturated or unsaturated carbonyl compounds, and aromatic and heteroaromatic carbonyl compounds. The carbonyl compounds for use as reactants may have one, two or more carbonyl groups. In addition, it is also possible to use carbonyl compounds which have heteroatoms, especially halogen atoms, such as chlorine, bromine, fluorine, oxygen, sulphur and/or nitrogen atoms in the aromatic or aliphatic radical. Particularly suitable carbonyl compounds preferably comprise 1 to 100, more preferably 2 to 20 and most preferably 2 to 5 carbon atoms.

The particularly preferred carbonyl compounds include aliphatic or heteroaliphatic ketones which have 3 to 5 carbon atoms, for example acetone, and aliphatic or heteroaliphatic aldehydes having 2 to 5 carbon atoms, for example 3-methylmercaptopropionaldehyde or acetaldehyde. Acetone is particularly preferred here as a reactant.

These compounds can be reacted individually or as a mixture with hydrogen cyanide (HCN) to give α-hydroxycarbonitriles (cyanohydrins), for example α-hydroxy-γ-methylthiobutyronitrile (2-hydroxy-4-methylthiobutyronitrile), 2-hydroxypropionitrile (lactonitrile) and 2-hydroxy-2-methylpropionitrile (acetone cyanohydrin), particular preference being given to acetone cyanohydrin.

The carbonyl compound is used in a molar excess, based on the hydrogen cyanide. The molar ratio of carbonyl compound to hydrogen cyanide may preferably be in the range from 1.1:1 to 7:1, preferably 1.5:1 to 5:1, and most preferably in the range from 2:1 to 3:1.

Preference is given to reacting the carbonyl compound with hydrogen cyanide in step A) in the presence of a base. It is possible here to use anion exchangers. Preference is given to using hydroxides or oxides, which are more preferably formed from alkaline earth metals or alkali metals. These include $Ca(OH)_2$ and $Mg(OH)_2$, MgO, CaO, NaOH, KOH, LiOH or $Li_2O$. Very particular preference is given here to using LiOH or $Li_2O$. Preferably 0.001 to 10% by weight, more preferably 0.01% by weight to 2% by weight, of hydroxide and/or oxide is added to the reaction mixture for reaction of the carbonyl compound with hydrogen cyanide. In a particular modification of the present invention, the proportion of hydroxide and/or oxide can be selected such that no further base need be added to adjust the pH of the subsequent hydrolysis reaction in step B).

Theoretically, it is also possible to use soluble amines to adjust the pH. However, it has been found that the use of these amines can have an adverse effect on the lifetime of the catalyst used for hydrolysis in step B). In addition to organic compounds with one nitrogen atom, ammonia ($NH_3$) is also included among the amines in the present context. The proportion of soluble amines in the reaction mixture is therefore preferably at most 0.1% by weight, more preferably at most 0.01% by weight and most preferably at most 0.001% by weight. In a particular aspect, no significant proportion of these amines is added to the reaction mixture to adjust the pH.

The temperature at which the reaction of the carbonyl compound with hydrogen cyanide is effected may generally be within the range from −30 to 70° C., preferably in the range from −20 to 60° C., especially in the range from −10 to 50° C. and more preferably in the range from −5 to 40° C.

The reaction in step A) to form a hydroxycarbonitrile can, according to the reaction temperature, be performed at reduced pressure or elevated pressure. This reaction is preferably performed within a pressure range from 0.5 to 10 bar, more preferably 0.8 to 3 bar.

The reaction time for formation of the hydroxycarbonitrile in step A) depends upon factors including the carbonyl compounds used, the activity of the catalyst and the reaction temperature, where these parameters may be within wide ranges. The reaction time for reaction of the carbonyl compound with HCN is preferably in the range from 30 seconds to 15 hours, more preferably 10 minutes to 5 hours and most preferably 30 minutes to 3 hours.

In continuous processes, the residence time of the reaction in step A) is preferably 30 seconds to 15 hours, more preferably 10 minutes to 5 hours and most preferably 30 minutes to 3 hours.

The reaction mixture prepared after the reaction in step A) is, in contrast to the prior art processes, not purified by distillation before the hydrolysis in step B) is performed. Distillation is understood here to mean a separation of the reaction mixture by virtue of different boiling points of the mixture constituents. This allows considerable efficiency improvements in the process to be achieved. In a particular configuration of the reaction in step A), no purification is needed. Instead, the mixture obtained after the reaction in step A) can be sent directly to a hydrolysis reaction in step B).

According to the invention, the hydrolysis of the carbonitrile obtained in step A) is performed in the presence of a catalyst comprising manganese dioxide. The stoichiometric composition of natural and synthetic manganese dioxide, by virtue of the incorporation of manganese of other valence states into the crystal lattice, may preferably be in the range between $MnO_{1.7}$ and $MnO_{2.0}$. Manganese dioxide exists in several allotropic polymorphs. They differ greatly in their behaviour as a catalyst. In pyrolysite (beta-manganese dioxide), the most stable polymorph, the crystallinity is the most marked. The crystallinity in the further polymorphs is less marked and extends down to amorphous products which include alpha- or delta-$MnO_2$. X-ray diffraction can assign the polymorphs. Some of the chemically and catalytically particularly active forms of manganese dioxide may be hydrated and additionally contain hydroxyl groups.

The catalyst comprising manganese dioxide may comprise further compounds or ions. These include especially alkali metal and/or alkaline earth metal ions which are introduced into the crystal lattice in the preparation or are deposited on the surface of the catalyst. The preferred alkali metal ions include especially lithium, sodium and/or potassium ions. The preferred alkaline earth metal ions include especially calcium and/or magnesium ions. The content of alkali metal and/or alkaline earth metal may preferably be less than 0.6 atom per atom of manganese. The atomic ratio of alkali metal and/or alkaline earth metal to manganese is preferably in the range from 0.01:1 to 0.5:1, more preferably in the range from 0.05:1 to 0.4:1.

In addition, the catalyst comprising manganese dioxide may comprise promoters, which may likewise be introduced into the crystal lattice or be deposited on the surface of the catalyst. The preferred promoters include Ti, Zr, V, Nb, Ta, Cr, Mo, W, Zn, Ga, In, Ge, Sn and Pt. The content of promoters may preferably be less than 0.3 atom per atom of manganese. The atomic ratio of promoter to manganese is preferably in the range from 0.001:1 to 0.2:1, more preferably in the range from 0.005:1 to 0.1:1. The catalyst comprising manganese dioxide may preferably comprise 0.01 to 10% by weight, more preferably 0.1 to 5% by weight, of promoters, this parameter being based on the weight measured as the metal or metal ion.

In addition, suitable catalysts may comprise fractions of $SiO_2$ or other binders in order to increase the mechanical stability, as detailed, for example, in EP-A-0 956 898.

Particularly preferred catalysts comprise, for example, 0.0 to 25% by weight, especially 0.1 to 2% by weight, of $SiO_2$;

0.1 to 10% by weight, especially 2 to 7% by weight, of $K_2O$;

0.0 to 5% by weight, especially 0.2 to 4% by weight, of $ZrO_2$ and 75 to 99% by weight, especially 85 to 98% by weight, of $MnO_2$. The catalyst may comprise further elements as has been detailed above. The composition of the catalysts can be determined by semiquantitative X-ray fluorescence analysis.

Preferred catalysts comprising manganese dioxide have, in the X-ray spectrum (XRD) measured as the powder, at least one reflection in the range from 32.0 to 42.0°. The X-ray spectra can be obtained, for example, with an Xpert pro system from Panalytical. This reflection in the range from 32.0 to 42.0° more preferably has the highest intensity in relation to the further intensities in the range from 20° to 65°, measured as the maximum of the reflection. Particularly preferred catalysts exhibit low crystallinity, and this can be seen, inter alia, from the X-ray spectrum. The structure of particularly preferred catalysts can be assigned to the structure number 44-0141 or 72-1982, which is presented in ICDD (International Centre for Diffraction Data), particular preference being given to the crystals having a structure according to 44-0141.

The alkali metal and/or alkaline earth metal ions and the promoters may be added, for example, in the form of salts in the preparation of the catalysts. For instance, it is possible in particular to use halides, nitrates, sulphates, carbonates, phosphates and hydroxides of the aforementioned substances, preference being given to using compounds which are soluble in water.

The catalyst comprising manganese dioxide may preferably comprise at least 50% by weight, more preferably at least 80% by weight, of manganese dioxide having an empirical formula $MnO_x$ where x is in the range from 1.7 to 2.0.

In a particular aspect of the present invention, the catalyst comprising manganese dioxide may have a specific surface area (BET) in the range from 50 to 1000 m² per g, more preferably 100 to 300 m² per g and most preferably 150 to 250 m² per g, which is determined according to test method DIN 66131.

Depending on the reactor type, the catalyst can be used, for example, in the form of powder or granule, the particle size in many cases being dependent upon the reaction vessel used.

The preparation of the catalysts which comprise manganese dioxide and have been described above is known per se and is detailed, for example, in EP-A-0 379 111, EP-A-0 956 898, EP-A-0545697 and EP-A-0 433 611. The catalysts which comprise manganese dioxide and are to be used in accordance with the invention can preferably be obtained by oxidation of $Mn^{2+}$ salts, for example $MnSO_4$, with permanganates, for example potassium permanganate (cf. Biochem. J., 50 p. 43 (1951) and J. Chem. Soc., p. 2189, 1953). In addition, suitable manganese dioxide can be obtained by electrolytic oxidation of manganese sulphate in aqueous solution.

Catalysts with structures according to 44-0141 can be obtained, for example, by adding an aqueous solution containing 0.71 mol of Mn(II) $SO_4$ (total of 15% by weight of $Mn^{2+}$ in solution), 0.043 mol of $Zr(IV)(SO_4)_2$, 0.488 mol of conc. sulphuric acid and 13.24 mol of water at 70° C. rapidly to a solution of 1.09 mol of $KMnO_4$ in 64.5 mol of water. The supernatant solution with the precipitate formed can be heated to 90° C. for 3 hours. The precipitate can then be filtered off, washed four times with one liter of water and dried at 110° C. for 12 hours.

The reaction mixture added to the catalyst comprising manganese dioxide preferably has a pH in the range from 6.0 to 11.0, preferably 6.5 to 10.0 and most preferably 8.5 to 9.5. In this context, the pH is defined as the negative decadic logarithm of the activity of the oxonium ions ($H_3O^+$). This parameter is thus dependent upon factors including the temperature, this parameter being based on the reaction temperature. For the purposes of the invention, it is in many cases sufficient to determine this parameter with electrical measuring units (pH meters), a determination at room temperature being sufficient for many purposes instead of the reaction temperature. The pH can preferably be adjusted as early as in the course of preparation of the hydroxycarbonitrile in step A), in which case the above-specified oxides and hydroxides can preferably be used.

It should be emphasized here that the catalyst comprising manganese dioxide in many cases has amphoteric properties; therefore, the pH of the reaction mixture in the reaction is greatly influenced by the type and amount of the catalyst. The expression "the reaction mixture added to the catalyst comprising manganese dioxide" makes it clear that the pH is measured without the presence of the catalyst. The further constituents of the reaction mixture include, for example, solvent, water, carbonitrile, etc.

It has been found that, surprisingly, hydrolysis in the presence of lithium ions leads to a particularly long lifetime of the catalyst comprising manganese dioxide. Accordingly, the process according to the invention can be further improved by adding lithium compounds, especially water-soluble lithium salts, to the reaction mixture, for example LiCl, LiBr, $Li_2SO_4$, LiOH and/or $Li_2O$. The concentration of lithium compounds is preferably in the range of 0.001 to 5% by weight, more preferably 0.01% by weight to 1% by weight. The addition can be effected during or before the hydrolysis reaction.

The hydrolysis of the carbonitrile to the carboxamide preferably takes place in the presence of an oxidizing agent. Suitable oxidizing agents are widely known in the technical field. These oxidizing agents include oxygenous gases; peroxides, for example hydrogen peroxide ($H_2O_2$), sodium peroxide, potassium peroxide, magnesium peroxide, calcium peroxide, barium peroxide, benzoyl peroxide and diacetyl peroxide; peracids or salts of peracids, for example performic acid, peracetic acid, sodium persulphate, ammonium persulphate and potassium persulphate; and oxo acids or salts of oxo acids, for example periodic acid, potassium periodate, sodium periodate, perchloric acid, potassium perchlorate, sodium perchlorate, potassium chlorate, sodium chlorate, potassium bromate, sodium iodate, iodic acid, sodium hypochlorite, permanganate salts, for example potassium permanganate, sodium permanganate and lithium permanganate, and salts of chromic acid, for example potassium chromate, sodium chromate and ammonium chromate.

The amount of the oxidizing agent used may be within a wide range, but the reactants and products should not be oxidized by the oxidizing agent. The oxidation sensitivity of these substances may therefore limit the use of the oxidizing agents. The lower limit results from the improvement in the service life of the catalyst to be achieved. The molar ratio of oxidizing agent to carbonitrile is preferably in the range of 0.001:1 to 2:1, more preferably 0.01:1 to 1.5:1.

These oxidizing agents may be added to the reaction mixture, for example, as a solution and/or as a gas. The oxidizing agents used are more preferably gases which comprise oxygen. In this case, the gas may comprise molecular oxygen ($O_2$) or ozone ($O_3$). In addition, the gas used as an oxidizing agent may comprise further gases, especially inert gases, such as nitrogen or noble gases. In a particular aspect, the gas may comprise preferably 50 to 98% by volume of inert gas and 2 to 50% by volume of molecular oxygen ($O_2$). The preferred gases include in particular air. In addition, it is also possible to use a gas which contains less than 20% by volume, in particular less than 10% by volume, of molecular oxygen, these gases containing generally at least 1% by volume, preferably at least 2% by volume, of oxygen.

The amount of gas which comprises oxygen and is passed through the reaction mixture may preferably be in the range of 1 to 5000 liters/hour, more preferably in the range of 10 to 1000 liters/hour, based on 1 kg of catalyst comprising manganese dioxide.

The water which is needed to hydrolyse the carbonitrile may in many cases be used as the solvent. The molar ratio of water to carbonitrile is preferably at least 1; the molar ratio of water to carbonitrile is more preferably in the range of 0.5:1-25:1 and most preferably in the range of 1:1-10:1.

The water used for the hydrolysis may have a high purity. However, this property is not obligatory. As well as fresh water, it is thus also possible to use service water or process water which comprises greater or lesser amounts of impurities. Accordingly, it is also possible to use recycled water for the hydrolysis.

In addition, further constituents may be present in the reaction mixture for the hydrolysis of the carbonitrile. These include carbonyl compounds such as aldehydes and ketones, especially those which have been used to prepare cyanohydrins to be used with preference as the carbonitrile. For example, acetone and/or acetaldehyde may be present in the reaction mixture. This is described, for example, in U.S. Pat. No. 4,018,829-A. The purity of the aldehydes and/or ketones added is generally not particularly critical. Accordingly, these substances may comprise impurities, especially alcohols, for example methanol, water and/or methyl α-hydroxyisobutyrate (MHIB). The amount of carbonyl compounds, especially acetone and/or acetaldehyde, may be used within wide ranges in the reaction mixture. The carbonyl compound is preferably used in an amount of 0.1-6 mol, preferably 0.1-2 mol, per mole of carbonitrile. In a particular modification of the present invention, this carbonyl compound may be added completely in step A), and so this excess is circulated.

The temperature at which the hydrolysis reaction is effected may generally be in the range of 10-150° C., preferably in the range of 20-100° C. and more preferably in the range of 30-80° C.

Depending on the reaction temperature, the hydrolysis reaction can be performed at reduced or elevated pressure. Preference is given to performing this reaction in a pressure range of 0.1-10 bar, more preferably 0.5 to 5 bar.

The reaction time of the hydrolysis reaction depends upon factors including the carbonitriles used, the activity of the catalyst and the reaction temperature, and these parameters may be within wide ranges. The reaction time of the hydrolysis reaction is preferably in the range of 30 seconds to 15 hours, more preferably 15 minutes to 10 hours and most preferably 60 minutes to 5 hours.

In continuous processes, the residence time is preferably 30 seconds to 15 hours, more preferably 15 minutes to 10 hours and most preferably 60 minutes to 5 hours.

The loading of the catalyst with carbonitrile may be within a wide range. Preference is given to using 0.01 to 2.0 g, more preferably 0.05 to 1.0 g and most preferably 0.1 to 0.4 g, of carbonitrile per g of catalyst per hour.

The reaction in step B) may be performed, for example, in a fixed bed reactor or in a suspension reactor. If gases are used as oxidizing agents, it is possible in particular to use so-called trickle bed reactors which enable good contact of gas, solid and liquid. In trickle bed reactors, the catalyst is arranged in the form of a fixed bed. In this case, the trickle bed reactor can be operated in cocurrent or countercurrent mode.

The reaction mixture obtained after step B) generally comprises, as well as the desired carboxamide, further constituents, especially unconverted carbonitrile or hydrogen cyanide, and carbonyl compound used in excess, especially acetone and/or acetaldehyde, and water used in excess.

Accordingly, the reaction mixture is generally separated in order to be able to reconvert the reactants already used. In a modification of the present invention, the reaction mixture obtained after step B) can be purified by a two-stage distillation.

The reaction mixture obtained after step B) generally still comprises proportions of hydroxycarbonitrile. The boiling point of the hydroxycarbonitrile is higher than that of water. Problems associated with this can be solved easily by a decomposition of the hydroxycarbonitrile to a carbonyl compound and hydrogen cyanide. This decomposition can be catalysed, for example, by the presence of a base, preferably of an anion exchanger, which is provided, for example, in the bottom of the still.

In a first modification of this preferred embodiment, in a first distillation step a), the resulting carboxamide can be separated from a mixture which comprises water, carbonyl compound and hydroxycarbonitrile and/or hydrogen cyanide. In this case, the hydroxycarbonitrile can preferably be split into carbonyl compound and hydrogen cyanide. The mixture thus obtained can be purified in a second distillation step b), in which case the carbonyl compound and the hydrogen cyanide can be withdrawn via the top and the water via the bottom of the second still.

The first distillation step a) for separation of the reaction mixture obtained in step B) into carboxamide and a mixture comprising water, carbonyl compound and hydroxycarbonitrile and/or hydrogen cyanide can preferably be performed at a temperature in the range from 110 to 260° C., more preferably in the range from 140 to 230° C. The pressure here is preferably in the range from 0.002 to 1 bar, more preferably in the range from 10 to 500 mbar. The distillation temperatures stated herein are based especially on the bottom temperature.

The temperature at which water is separated from carbonyl compound and hydrogen cyanide in step b) may generally be in the range from 50 to 150° C., preferably in the range from 70 to 120° C. and more preferably in the range from 90 to 110° C. The second distillation step b) can preferably be performed within a pressure range from 0.2 to 5 bar, more preferably 0.7 to 1.5 bar.

In a particularly preferred embodiment, the carbonyl compound and hydrogen cyanide can first be removed via the top in a first distillation step a') from the reaction mixture obtained after step B).

In this case, hydroxycarbonitrile is first separated into carbonyl compound and hydrogen cyanide, and in this way is likewise removed from the mixture via the top. The hydrogen cyanide and carbonyl compound obtained in this way can be used to prepare hydroxycarbonitrile in step A). The mixture obtained from the bottoms comprises water and carboxamide. This mixture is separated in a second step b'), wherein the carboxamide can advantageously be separated from water in a multistage evaporative concentration, also known as multistage evaporation. In this case, the amount of vapour generated by primary energy is used in a second stage at a lower pressure level as a heating medium for the liquid phase. This principle can be continued over several stages for energy saving. Advantageously, a multistage evaporative concentration comprises 2 to 4 of these separation stages. The principle of multistage evaporative concentration is described in more detail in publications including H. G. Hirschberg, Handbuch der Verfahrenstechnik and des Anlagenbau [Handbook of Process Technology and of Plant Construction], Springer 1999, reference being made to this document for disclosure purposes. This configuration surprisingly enables a particularly energy-efficient purification of the reaction mixture obtained in step B). The resulting water can be used for hydrolysis in step B).

The first distillation step a') for separation of the reaction mixture obtained in step B) into carboxamide and water, and a mixture comprising carbonyl compound and hydrogen cyanide, can preferably be performed at a temperature in the range from 50 to 170° C., more preferably in the range from 90 to 120° C. The pressure in this step a') is preferably in the range from 0.4 to 5 bar, more preferably in the range from 0.7 to 2 bar. The distillation temperatures stated herein relate especially to the bottom temperature.

The temperature at which water and carboxamide can be separated in step b') may generally be within the range from 90 to 260° C., preferably within the range from 100 to 180° C. The second distillation step b') can preferably be performed within a pressure range from 10 mbar to 20 bar, more preferably 100 mbar to 10 bar. High pressure values apply especially to the first stages of a multistage evaporative concentration.

Surprising advantages with regard to the service life of the plant and the lifetime of the catalyst can be achieved especially by virtue of a composition comprising the carbonyl compound used in step A) being introduced via the reflux into the still used to separate water and hydrogen cyanide, the composition introduced into the reflux having a lower proportion of HCN than the composition withdrawn via the top of the still. The proportion by weight of HCN in the composition which is introduced into the reflux is preferably at most 60%, more preferably at most 40% and most preferably at most 10% of the amount of HCN present in the composition withdrawn via the top of the still, based on the weight. The composition introduced into the reflux of the still more preferably comprises essentially no HCN. In this connection, it should be emphasized that hydroxycarbonitrile can form from the carbonyl compound and hydrogen cyanide removed, and likewise should not be recycled into the still. Accordingly, the figures stated above with regard to the amount of HCN which is returned to the still refer to the sum of the amounts of free HCN and of HCN bound in the form of hydroxycarbonitrile. The amount of bound HCN can be determined by decomposing the hydroxycarbonitrile. Accordingly, the composition introduced into the reflux of the still also comprises essentially no hydroxycarbonitrile.

In a preferred modification of the present invention, the carbonyl compound removed in the course of separation of water and hydrogen cyanide is used to prepare a hydroxycarbonitrile in step A). Accordingly, the top product of the corresponding distillation step is preferably used to prepare the hydroxycarbonitrile used in step B). Accordingly, the water obtained can be used for hydrolysis of the hydroxycarbonitrile in step B).

A further improvement in the lifetime of the catalyst can be achieved especially through the use of a column with a high separating performance, especially in the separation of water and hydrogen cyanide. Accordingly, preferably one distillation column which has two or more separating stages is used for this purpose. In the present invention, the number of separating stages refers to the number of trays in a tray column or the number of theoretical plates in the case of a column with structured packing or a column with random packing.

Examples of multistage distillation columns with trays include those such as bubble-cap trays, sieve trays, tunnel-cap trays, valve trays, slot trays, slotted sieve trays, bubble-cap sieve trays, jet trays, centrifugal trays; for a multistage distillation column with random packing, those such as Raschig rings, Lessing rings, Pall rings, Berl saddles, Intalox saddles; and, for a multistage distillation column with structured packings, those such as the Mellapak (Sulzer), Rombopak (Kühni), Montz-Pak (Montz) types and structured packings with catalyst pockets, for example Kata-Pak.

A distillation column with combinations of regions of trays, of regions of random packings or of regions of structured packings can likewise be used.

The use of a distillation column with a high separating performance and of a reflux with a low hydrogen cyanide content allows the proportion of HCN in the aqueous phase which is used for the hydrolysis to be kept very low. Preference is given to recycling to the hydrolysis an aqueous phase which comprises only exceptionally low proportions of hydrogen cyanide, it being possible to achieve especially values less than 1% by weight, more preferably less than 0.5% by weight and more preferably less than 0.1% by weight of hydrogen cyanide, based on the aqueous phase recycled.

Surprising advantages can be achieved especially by virtue of the amount of carbonyl compound added in the distillation step to separate water and hydrogen cyanide being selected such that it is sufficient to prepare the amount of hydroxycarbonitrile envisaged in step A). Accordingly, the carbonyl compound required for conversion of HCN is preferably added fully to the reflux of the still which is used to distil a mixture which comprises water, HCN and the carbonyl compound used in step A). According to the configuration, this can be done in the first or second distillation.

In addition, the reaction mixture comprising purified carboxamide can be purified to remove further constituents by means of ion exchange columns.

To this end, it is possible to use especially cation exchangers and anion exchangers. Ion exchangers suitable for this purpose are known per se. For example, it is possible to obtain suitable cation exchangers by sulphonating styrene-divinylbenzene copolymers. Basic anion exchangers comprise quaternary ammonium groups which are bonded covalently to styrene-divinylbenzene copolymers.

The purification of α-hydroxycarboxamides is described in more detail, inter alia, in EP-A-0686623.

The hydrolysis reaction of the present invention may in particular serve as an intermediate step in processes for preparing (meth)acrylic acids. The term "(meth)acrylic monomers" embraces methacrylic monomers and acrylic monomers and mixtures of the two. The term "(meth)acrylic monomers" includes, especially, (meth)acrylic acids, in particular acrylic acid (propenoic acid) and methacrylic acid (2-methylpropenoic acid) and the esters of these acids, also referred to as (meth)acrylates. Accordingly, the present invention also provides a process for preparing alkyl (meth)acrylates, especially methyl methacrylate, which has a hydrolysis step according to a process of the present invention. Processes which may have a hydrolysis step of cyanohydrins to prepare (meth)acrylic acid and/or alkyl (meth)acrylates are detailed, inter alia, in EP-A-0 406 676, EP-A-0 407 811, EP-A-0 686 623 and EP-A-0 941 984.

In a particularly preferred embodiment, it is possible to obtain alkyl (meth)acrylates from carbonyl compounds, hydrogen cyanide and alcohols in a simple and inexpensive manner by processes which comprise the following steps:

A) formation of at least one cyanohydrin by reacting at least one carbonyl compound with hydrogen cyanide;
B) hydrolysis of the cyanohydrin or of the cyanohydrins to form at least one α-hydroxycarboxamide;
C) alcoholysis of the α-hydroxycarboxamide or of the α-hydroxycarboxamides to obtain at least one alkyl α-hydroxycarboxylate;
D) transesterification of the alkyl α-hydroxycarboxylate or of the alkyl α-hydroxycarboxylates with (meth)acrylic acid to form at least one alkyl (meth)acrylate and at least one α-hydroxycarboxylic acid;
E) dehydration of the α-hydroxycarboxylic acid or of the α-hydroxycarboxylic acids to form (meth)acrylic acid.

Steps A) and B) have been explained in detail above. In the next step C), the α-hydroxycarboxamide thus obtained can be converted to the alkyl α-hydroxycarboxylate. This can be done, for example, by the use of alkyl formates. An especially suitable reactant is methyl formate or a mixture of methanol and carbon monoxide, this reaction being described by way of example in EP-A-0407811.

Preference is given to reacting the α-hydroxycarboxamide by alcoholysis with an alcohol which comprises preferably 1-10 carbon atoms, more preferably 1 to 5 carbon atoms. Preferred alcohols include methanol, ethanol, propanol, butanol, especially n-butanol and 2-methyl-1-propanol, pentanol, hexanol, heptanol, 2-ethylhexanol, octanol, nonanol and decanol. The alcohol used is more preferably methanol and/or ethanol, very particular preference being given to methanol. The reaction of carboxamides with alcohols to obtain carboxylic esters is common knowledge.

The molar ratio of α-hydroxycarboxamide to alcohol, for example α-hydroxyisobutyramide to methanol, is not critical per se, and is preferably in the range from 3:1 to 1:20. This ratio is very particularly appropriately in the range from 2:1 to 1:15 and more preferably in the range from 1:1 to 1:10.

The reaction temperature may likewise be within wide ranges, the reaction rate generally increasing with increasing temperature. The upper temperature limit arises generally from the boiling point of the alcohol used. The reaction temperature is preferably in the range from 40-300° C., more preferably 160-240° C. The reaction may, depending on the reaction temperature, be performed at reduced or elevated pressure. This reaction is preferably performed in a pressure range of 0.5-200 bar, particularly appropriately in a range of 1 to 100 bar and more preferably 5 to 30 bar.

In a particular embodiment, the reaction between alpha-hydroxycarboxamide and alcohol can be performed in a pressure reactor. This is in principle understood to mean a reaction chamber which permits an elevated pressure to be maintained during the reaction. In this context, elevated pressure means a pressure greater than atmospheric pressure, i.e. in particular greater than 1 bar. The pressure may preferably be in the range from greater than 1 bar to less than 100 bar. Accordingly, the pressure, both during the reaction/alcoholysis of alpha-hydroxycarboxamide and during the removal of the ammonia from the product mixture, may be greater than atmospheric pressure or greater than 1 bar. Therefore, the ammonia formed in the reaction can be distilled out of the mixture under a pressure of greater than 1 bar, and it is possible to completely dispense with the use of aids such as stripping gas for the distillative removal of the ammonia.

The product mixture may be depleted not only in ammonia but also in unconverted alcohol. Specifically in the case that methanol is used for the alcoholysis, the result is a product mixture comprising, inter alia, the ammonia and methanol components which are in principle very difficult to separate from one another. In the simplest case, the product mixture is depleted of ammonia and alcohol by removing said two components directly as a substance mixture from the product mixture. The two substances are then subjected to a separating operation, for example a rectification. In addition, the two components alcohol (methanol) and ammonia can be separated from the product mixture in one operation, and the two constituents ammonia and alcohol (methanol) can at the same time be separated from one another.

The reaction step and the removal of the ammonia/alcohol from the product mixture can be performed spatially separately from one another and in different units. For this purpose, it is possible, for example, to provide one or more pressure reactors and to connect them to a pressure distillation column. This system comprises one or more reactors which are arranged outside the column in a separate region.

Preference may be given to employing a continuous process for preparing alpha-hydroxycarboxylic esters in which alpha-hydroxycarboxamide reactants are reacted with an alcohol in the presence of a catalyst to obtain a product mixture which comprises alpha-hydroxycarboxylic ester, ammonia, unconverted alpha-hydroxycarboxamide, and alcohol and catalyst; by a') feeding reactant streams comprising, as reactants, an alpha-hydroxycarboxamide, an alcohol and a catalyst into a pressure reactor;
b') reacting the reactant streams with one another in the pressure reactor at a pressure in the range from greater than 1 bar to 100 bar;
c') discharging the product mixture which results from step b') and comprises alpha-hydroxycarboxylic ester, unconverted alpha-hydroxycarboxamide and catalyst from the pressure reactor; and
d') depleting the product mixture in alcohol and ammonia, ammonia being distilled off at a pressure which is constantly kept greater than 1 bar.

In this case, a particularly appropriate process modification can be provided by b1) reacting the reactants with one another in the pressure reactor at a pressure in the range from 5 bar to 70 bar;
b2) decompressing the product mixture resulting from step b1) to a pressure less than the pressure in the pressure reactor and greater than 1 bar;
c1) feeding the decompressed product mixture which results from step b2) into a distillation column;
c2) in the distillation column, distilling off ammonia and alcohol via the top, the pressure in the distillation column being kept in the range from greater than 1 bar to less than 10 bar; and
d1) discharging the product mixture which results from step c2), has been depleted of ammonia and alcohol, and comprises alpha-hydroxycarboxylic ester, unconverted alpha-hydroxycarboxamide and catalyst from the column.

In this preferred process variant, reaction of the reactants and removal of ammonia/alcohol take place in two different spatially separate units. In other words, reactor/reaction chamber and separating unit for the removal of ammonia/alcohol from the product mixture are separated from one another. This has the advantage that, for the reaction of the reactants and the subsequent removal of ammonia/alcohol, different pressure ranges can be employed. The separation of the process into a reaction step in the pressure reactor under higher pressure than in a separating step in a pressure column, both steps being conducted under elevated pressure, i.e. greater than 1 bar, surprisingly allows the separating action to be improved significantly once more and the efficiency of the removal of the ammonia/alcohol mixture to be increased.

The quality features mentioned can be improved even further by repeating the reaction in the pressure reactor once or more than once with the product mixture which has been depleted of ammonia and alcohol in the bottom of the separating column (pressure distillation column), the reaction step being shifted to a multitude of pressure reactors which are connected in series.

In this respect, very particular preference is given to a process variant which is characterized in that e) the product mixture discharged in step d1) is compressed to a pressure in the range from 5 to 70 bar;
f) the mixture compressed in this way in step e) is fed into a further pressure reactor for reaction and allowed to react again; and
g) steps b2), c1), c2) and d1) are repeated according to the list above.

Accordingly, it is of particular interest that the ammonia- and alcohol-depleted mixture is withdrawn from a tray above the bottom of the first distillation column, compressed to a pressure greater than in the distillation column and then fed into a second pressure reactor, whence, after another reaction under the action of elevated pressure and temperature to obtain a twice-reacted product mixture, it is in turn decompressed to a pressure less than in the second pressure reactor and greater than 1 bar, and then recycled into the first distillation column below the tray from which the feeding into the second pressure reactor was effected but above the bottom of the first distillation column, where ammonia and alcohol are distilled off again via the top to obtain a mixture depleted twice in ammonia and alcohol.

This process step can be repeated as desired; for example, three to four repetitions are particularly favourable. In this respect, preference is given to a process which is characterized in that the reaction in the pressure reactor, the decompression of the reacted mixture, the feeding into the first distillation column, the depletion of ammonia and alcohol in the first distillation column, the withdrawal of the depleted mixture, compression and feeding of the depleted mixture into a further pressure reactor are repeated more than once to obtain, depending on the number n of pressure reactors connected in series, a product mixture depleted n times in ammonia and alcohol at the bottom of the pressure distillation column. In this context, n may be a positive integer greater than zero. n is preferably in the range from 2 to 10.

An appropriate process modification envisages repeating the steps e) to g) mentioned and defined above more than once.

Very specific process variants comprise the performance of the reaction and depletion four times using four pressure reactors connected in series to obtain a product mixture depleted four times in ammonia and alcohol. This process variant is accordingly characterized in that steps e) to g) are repeated at least twice more, so that the reaction is performed in a total of at least four pressure reactors connected in series.

For the process variant specified, different temperature ranges have been found to be particularly appropriate in column and reactor.

For example, the pressure distillation column may generally and preferably have a temperature in the range from about 50° C. to about 160° C. The exact temperature is typically established by the boiling system as a function of the existing pressure conditions.

The temperature in the reactor is preferably in the range from about 120-240° C. It is very particularly appropriate to lower the temperature from reactor to reactor, for example in steps in the range from 3-15° C., preferably 4-10° C. and very particularly appropriately in steps of 5° C. This positively influences the selectivity of the reaction.

A further measure for increasing the selectivity may also consist in decreasing the reactor volume from reactor to reactor. Decreasing reactor volume with increasing conversion likewise affords improved selectivity.

As already mentioned above, it is favourable to withdraw the product mixture to be withdrawn from the pressure distillation column at certain points in the column. In this context, for orientation, as a relative statement of location, the distance of the withdrawal point from the bottom of the column is used. Particularly appropriately, the procedure in the context of the invention is to feed the decompressed product mixture according to step c1) after each new reaction into a pressure reactor more closely adjacent to the bottom of the distillation column based on the feed point of the feeding of the preceding step c1).

In addition to the variant described, in which the reaction of the alpha-hydroxycarboxamide with the alcohol is performed by the removal of the ammonia which is one resulting product in two spatially separate but connected units, it may be preferred in a further process modification to undertake the reaction step and the removal step in a single unit. In this case, pressure reactor and pressure distillation column are realized in a single unit, and effectively coincide.

The pressure range to be observed in the inventive variant described above, preferably in a reactive distillation column serving as a reactor, is variable over wide ranges. A preferred embodiment of the invention comprises the performance of steps a) to c) simultaneously in a reactive distillation column at a pressure in the range from 5 bar to 40 bar. A particularly appropriate process is one which is characterized in that steps a) to c) are performed simultaneously in a reactive distillation column at a pressure in the range from 10 bar to 30 bar.

In a preferred variant of the process, the reaction of the reactants is performed in a reactive distillation column designed as a pressure column, and the ammonia formed is distilled off continuously via the top of the column during the reaction. This achieves the surprising effect that ammonia can be removed in a very simple manner without needing to reduce the pressure and can be recovered in high purity. Another variant of particular interest is one in which ammonia is distilled off under pressure via the top of the column and the alcohol is removed from the column via the bottom or via a sidestream. As a result of an appropriately configured separating action of the reactive distillation column, immediate separation of ammonia and alcohol is thus achieved.

For the present invention, in one variant, any multistage pressure-resistant reactive distillation column which preferably has two or more separating stages can be used. Such reactive stills are explained in detail in connection with step D), and these can also be used for the reaction of the carboxamide with an alcohol.

The ammonia-depleted product mixture contains, inter alia, the desired alpha-hydroxycarboxylic ester. To further isolate and purify the ester, it is possible in an appropriate process modification to draw off the ammonia-depleted product mixture via the bottom of the reactive distillation column and to feed it to a further second distillation column, where the alcohol is distilled off via the top of the column and preferably recycled into a reactor to obtain a mixture depleted of both ammonia and alcohol.

To further isolate and recover the alpha-hydroxycarboxylic ester from the ammonia- and alcohol-depleted mixture, preference is then given to a process in which the ammonia- and alcohol-depleted mixture is discharged via the bottom of the further distillation column and fed to yet a further distillation column in which the alpha-hydroxycarboxylic ester is distilled off via the top and the thus obtained mixture depleted of ammonia, alcohol and alpha-hydroxycarboxylic ester, optionally after further purification steps, is recycled into the reactor. The alpha-hydroxycarboxylic ester product obtained via the top of the column is highly pure and can, for example, be fed extremely advantageously to further reaction steps to obtain alkyl (meth)acrylates.

As outlined, the distillation apparatus preferably has at least one region, known as reactor, in which at least one catalyst is provided. This reactor can, as described, preferably be within the distillation column.

For the invention, it may be advantageous when at most 10% by weight, preferably at most 5% by weight and more preferably at most 1% by weight of the alcohol present in the reaction phase is removed from the reaction system via the gas phase. This measure allows the reaction to be performed particularly inexpensively.

This reaction can be accelerated, for example, by basic catalysts. These include homogeneous catalysts and heterogeneous catalysts.

The homogeneous catalysts include alkali metal alkoxides and organometallic compounds of titanium, tin and aluminium. Preference is given to using a titanium alkoxide or tin alkoxide, for example titanium tetraisopropoxide or tin tetrabutoxide. The heterogeneous catalysts include magnesium oxide, calcium oxide and basic ion exchangers as have been described above.

Catalysts of very particular interest for the performance of the process according to the invention are water-stable lanthanoid compounds. The use of this type of homogeneous catalysts leads to surprisingly advantageous results. The expression "water-stable" means that the catalyst retains its catalytic abilities in the presence of water. Accordingly, the inventive reaction can be effected in the presence of up to 2% by weight of water without this significantly impairing the catalytic ability of the catalyst. In this context, the expression "significantly" means that the reaction rate and/or selectivity decreases at most by 50% based on the reaction without the presence of water.

Lanthanoid compounds denote compounds of La, Ce, Pr, Nd, Pm, Sm, Eu, Gd, Tb, Dy, Ho, Er, Tm, Yb and/or Lu. Preference is given to using a lanthanoid compound which comprises lanthanum. The lanthanoid compound preferably has a solubility in water of at least 1 g/l, preferably at least 10 g/l, at 25° C. Preferred lanthanoid compounds are salts which are preferably present in the oxidation state of 3. Particularly preferred water-stable lanthanoid compounds are $La(NO_3)_3$ and/or $LaCl_3$. These compounds may be added to the reaction mixture as salts or be formed in situ.

A particular process variant includes the use, as a catalyst, of a soluble metal complex which comprises titanium and/or tin and the alpha-hydroxycarboxamide.

Another specific modification of the invention envisages the use of a metal trifluoromethanesulphonate as a catalyst. In this case, preference is given to using a metal trifluoromethanesulphonate in which the metal is selected from the group consisting of the elements in groups 1, 2, 3, 4, 11, 12, 13 and 14 of the Periodic Table. Among these, preference is given to using those metal trifluoromethanesulphonates in which the metal corresponds to one or more lanthanoids.

In addition to the preferred variants of homogeneous catalysis, processes using heterogeneous catalysts are also appropriate under some circumstances. The successfully usable heterogeneous catalysts include magnesium oxide, calcium oxide and basic ion exchangers, and the like. For example, preference may be given to processes in which the catalyst is an insoluble metal oxide which comprises at least one element selected from the group consisting of Sb, Sc, V, La, Ce, Ti, Zr, Hf, V, Nb, Ta, Cr, Mo, W, Tc, Re, Fe, Co, Ni, Cu, Al, Si, Sn, Pb and Bi. Alternatively, preference may be given to processes where the catalyst used is an insoluble metal selected from the group consisting of Ti, Zr, Hf, V, Nb, Ta, Cr, Mo, W, Fe, Co, Ni, Cu, Ga, In, Bi and Te.

Typically, the ammonia formed is discharged from the reaction system, the reaction in many cases being performed at the boiling point.

The ammonia released in the alcoholysis may be recycled easily to the overall process. For example, ammonia may be reacted with methanol to give hydrogen cyanide. This is detailed, for example, in EP-A-0941984. In addition, the hydrogen cyanide can be obtained from ammonia and methane by the BMA or Andrussow processes, these processes being described in Ullmann's Encyclopedia of Industrial Chemistry, 5th Edition on CD-ROM, under "Inorganic Cyano Compounds".

Preferred configurations of the alcoholysis of the α-hydroxycarboxamide in step C) are described in WO 2007/131829, filed at the European Patent Office with application number PCT/EP2007/052951 on Mar. 28, 2007, the embodiments described herein of the reaction of the hydroxycarboxamide with an alcohol being incorporated into the present application for the purposes of disclosure.

In a next step D), the alkyl α-hydroxycarboxylate is reacted with (meth)acrylic acid to obtain alkyl (meth)acrylate and α-hydroxycarboxylic acid.

In the further aspect of the present invention, alkyl α-hydroxycarboxylates can be reacted with (meth)acrylic acid. The (meth)acrylic acids usable for this purpose are known per se and can be obtained commercially. In addition to acrylic acid (propenoic acid) and methacrylic acid (2-methylpropenoic acid), these include in particular derivatives which comprise substituents. The suitable substituents include in particular halogens such as chlorine, fluorine and bromine, and alkyl groups which may comprise preferably 1 to 10, more preferably 1 to 4 carbon atoms. These include β-methylacrylic acid (butenoic acid), α,β-dimethylacrylic acid, β-ethylacrylic acid and β,β-dimethylacrylic acid. Preference is given to acrylic acid (propenoic acid) and methacrylic acid (2-methylpropenoic acid), particular preference being given to methacrylic acid.

The alkyl α-hydroxycarboxylates used for this purpose are known per se, the alcohol radical of the ester comprising preferably 1 to 20 carbon atoms, in particular 1 to 10 carbon atoms and more preferably 1 to 5 carbon atoms. Preferred alcohol radicals derive in particular from methanol, ethanol, propanol, butanol, in particular n-butanol and 2-methyl-1-propanol, pentanol, hexanol and 2-ethylhexanol, particular preference being given to methanol and ethanol.

The acid radical of the alkyl α-hydroxycarboxylates used for the transesterification derives preferably from the (meth)acrylic acid which can be obtained by dehydrating the α-hydroxycarboxylic acid. When, for example, methacrylic acid is used, α-hydroxyisobutyric ester is used. When, for example, acrylic acid is used, preference is given to using α-hydroxyisopropionic acid.

Alkyl α-hydroxycarboxylates used with preference are methyl α-hydroxypropionate, ethyl α-hydroxypropionate, methyl α-hydroxyisobutyrate and ethyl α-hydroxyisobutyrate.

In addition to the reactants, the reaction mixture may comprise further constituents, for example solvents, catalysts, polymerization inhibitors and water.

The reaction of alkylhydroxycarboxylic ester with (meth)acrylic acid can be catalysed by at least one acid or at least one base. It is possible to use either homogeneous or heterogeneous catalysts. Particularly suitable acidic catalysts are in particular inorganic acids, for example sulphuric acid or hydrochloric acid, and organic acids, for example sulphonic acids, in particular p-toluenesulphonic acid, and acid cation exchangers.

The particularly suitable cation exchange resins include in particular sulphonic acid-containing styrene-divinylbenzene polymers. Particularly suitable cation exchange resins can be obtained commercially from Rohm & Haas under the trade name Amberlyst® and from Lanxess under the trade name Lewatit®.

The concentration of catalyst is preferably in the range from 1 to 30% by weight, more preferably 5 to 15% by weight, based on the sum of the α-alkylhydroxycarboxylic ester used and of the (meth)acrylic acid used.

The polymerization inhibitors usable with preference include phenothiazine, tert-butylcatechol, hydroquinone monomethyl ether, hydroquinone, 4-hydroxy-2,2,6,6-tetramethylpiperidinooxyl (TEMPOL) or mixtures thereof; the effectiveness of these inhibitors can be improved in some cases by using oxygen. The polymerization inhibitors may be used in a concentration in the range from 0.001 to 2.0% by weight, more preferably in the range from 0.01 to 0.2% by weight, based on the sum of the α-alkylhydroxycarboxylic ester used and of the (meth)acrylic acid used.

The reaction is performed preferably at temperatures in the range from 50° C. to 200° C., more preferably 70° C. to 130° C., in particular 80° C. to 120° C. and most preferably 90° C. to 110° C.

The reaction can be performed at reduced or elevated pressure depending on the reaction temperature. This reaction is preferably performed in the pressure range of 0.02-5 bar, in particular 0.2 to 3 bar and more preferably 0.3 to 0.5 bar.

The molar ratio of (meth)acrylic acid to the alkyl α-hydroxycarboxylate is preferably in the range from 4:1-1:4, in particular 3:1 to 1:3 and more preferably in the range from 2:1-1:2.

The selectivity is preferably at least 90%, more preferably 98%. The selectivity is defined as the ratio of the sum of amounts of alkyl (meth)acrylates and α-hydroxycarboxylic acids formed based on the sum of the amounts of alkyl α-hydroxycarboxylates and (meth)acrylic acid converted.

In a particular aspect of the present invention, the transesterification can be effected in the presence of water. The water content is preferably in the range from 0.1-50% by weight, more preferably 0.5-20% by weight and most preferably 1-10% by weight, based on the weight of the alkyl α-hydroxycarboxylate used.

The addition of small amounts of water surprisingly allows the selectivity of the reaction to be increased. In spite of water addition, the formation of methanol can be kept surprisingly low. At a water concentration of 10 to 15% by weight based on the weight of the alkyl α-hydroxycarboxylate used, preferably less than 5% by weight of methanol forms at a reaction temperature of 120° C. and a reaction time or residence time of 5 to 180 min.

The transesterification can be performed batchwise or continuously, preference being given to continuous processes. In the transesterification, the products can preferably be removed from the reactants in order to shift the equilibrium of the reaction.

The reaction time of the transesterification depends upon the molar masses used and on the reaction temperature, and these parameters may be within wide ranges. The reaction time of the transesterification of the alkyl α-hydroxycarboxylate with (meth)acrylic acid is preferably in the range from 30 seconds to 15 hours, more preferably 5 minutes to 5 hours and most preferably 15 minutes to 3 hours.

In continuous processes, the residence time is preferably 30 seconds to 15 hours, more preferably 5 minutes to 5 hours and most preferably 15 minutes to 3 hours.

In the preparation of methyl methacrylate from methyl α-hydroxyisobutyrate, the temperature is preferably 60 to 130° C., more preferably 80 to 120° C. and most preferably 90 to 110° C. The pressure is preferably in the range from 50 to 1000 mbar, more preferably 300 to 800 mbar. The molar ratio of methacrylic acid to methyl α-hydroxyisobutyrate is preferably in the range from 2:1-1:2, in particular 1.5:1-1:1.5.

In a particularly preferred embodiment, the transesterification can be effected in a still. In this case, the catalyst can be added in any region of the still. For example, the catalyst can be provided in the region of the bottom or in the region of the column. At the same time, however, the reactants should be brought into contact with the catalyst. In addition, catalysts may be provided in a separate region of the still, in which case this region is connected to the further regions of the still, for example the bottom and/or the column. This separate arrangement of the catalyst region is preferred.

This preferred embodiment surprisingly succeeds in increasing the selectivity of the reaction. In this context, it should be emphasized that the pressure of the reaction can be adjusted independently of the pressure within the distillation columns. This allows the boiling temperature to be kept low without the reaction time or the residence time rising correspondingly. In addition, the temperature of the reaction can be varied over a wide range. This allows the reaction time to be shortened. In addition, the volume of catalyst can be selected as desired without needing to take account of the geometry of the column. Furthermore, for example, a further reactant can be added. All of these measures can contribute to the increase in the selectivity and the productivity, surprising synergistic effects being achieved.

In this process, the alkyl α-hydroxycarboxylate, for example methyl α-hydroxyisobutyrate, is fed to the still. In addition, (meth)acrylic acid, for example methacrylic acid, is introduced into the still. The distillation conditions are preferably configured in such a way that exactly one product is discharged from the still by distillation, the second product remaining in the bottom and being removed continuously therefrom. In the case of use of alcohols with a low carbon number, especially ethanol or methanol, preference is given to withdrawing the alkyl (meth)acrylate from the reaction mixture by distillation. The reactants are passed cyclically through the catalyst region. This continuously forms alkyl (meth)acrylate and α-hydroxycarboxylic acid.

A preferred embodiment of a still is shown schematically in FIG. 1. The reactants may be introduced into the distillation column (3) via one common line (1) or separately via two lines (1) and (2). The reactants are preferably added via separate lines. The reactants can be fed to the column at the same stage or in any position.

The temperature of the reactants can be adjusted by means of a heat exchanger in the feed, the units needed for this purpose not being shown in FIG. 1. In a preferred variant, the reactants are metered separately into the column, the lower-boiling component being metered in below the position for the feeding of the higher-boiling compound. In this case, the lower-boiling component is preferably added in vaporous form.

For the present invention, any multistage distillation column (3) which has two or more separating stages may be used. The number of separating stages used in the present invention is the number of trays in a tray column or the number of theoretical plates in the case of a column with structured packing or a column with random packings.

Examples of a multistage distillation column with trays include those such as bubble-cap trays, sieve trays, tunnel-cap trays, valve trays, slot trays, slotted sieve trays, bubble-cap sieve trays, jet trays, centrifugal trays; for a multistage distillation column with random packings, those such as Raschig rings, Lessing rings, Pall rings, Berl saddles, Intalox saddles; and, for a multistage distillation column with structured packings, those such as the Mellapak (Sulzer), Rombopak (Kühni), Montz-Pak (Montz) types and structured packings with catalyst pockets, for example Kata-Pak.

A distillation column with combinations of regions of trays, of regions of random packings or of regions of structured packings may likewise be used.

The column (3) may be equipped with internals. The column preferably has a condenser (12) for condensing the vapour and a bottom evaporator (18).

The distillation apparatus preferably has at least one region, known hereinafter as reactor, in which at least one catalyst is provided. This reactor may be within the distillation column. However, this reactor is preferably arranged outside the column (3) in a separate region, one of these preferred embodiments being explained in detail in FIG. 1.

In order to carry out the transesterification reaction in a separate reactor (8), it is possible within the column to collect a portion of the liquid phase flowing downwards by means of a collector and to pass it out of the column as a substream (4). The position of the collector is determined by the concentration profile in the column of the individual components. The concentration profile can be regulated by means of the temperature and/or the reflux. The collector is preferably positioned such that the stream conducted out of the column contains both reactants, more preferably the reactants in sufficiently high concentration and most preferably in a molar acid:ester ratio=1.5:1 to 1:1.5. In addition, a plurality of collectors may be provided at various points in the distillation column, in which case the amount of reactants withdrawn can be used to adjust the molar ratios.

It is additionally possible for a further reactant, for example water, to be metered into the stream conducted out of the column, in order to adjust the acid/ester product ratio in the cross-transesterification reaction or to increase the selectivity. The water can be fed from outside via a line (not shown in FIG. 1) or withdrawn from a phase separator (13). The pressure of the stream (5) enriched with water can then be increased by a means for pressure increase (6), for example a pump.

An increase in the pressure can reduce or prevent formation of steam in the reactor, for example a fixed bed reactor. This allows uniform flow through the reactor and wetting of the catalyst particles. The stream can be conducted through a heat exchanger (7) and the reaction temperature adjusted. The stream can be heated or cooled as required. It is additionally possible to adjust the ester to acid product ratio via the reaction temperature.

The transesterification reaction takes place over the catalyst in the fixed bed reactor (8). The flow through the reactor may be downwards or upwards. The reactor output stream (9) comprising the products and the unconverted reactants to a certain degree, the content of the components in the reactor waste stream depending upon the residence time, the catalyst mass, the reaction temperature and the reactant ratio and the amount of water added, is first passed through a heat exchanger (10) and adjusted to a temperature which is advantageous for the introduction into the distillation column. Preference is given to setting the temperature which corresponds to the temperature in the distillation column at the point of introduction of the stream.

The position where the stream leaving the reactor is returned into the column may lie above or below the position for the withdrawal of the reactor feed, but will preferably be above it. Before the recycling into the column, the stream may be decompressed through a valve (11), which preferably establishes the same pressure level as in the column. In this context, the distillation column preferably has a lower pressure. This configuration offers the advantage that the boiling points of the components to be separated are lowered, as a result of which the distillation can be carried out at a lower temperature level, as a result of which it saves energy and is more thermally gentle.

In the distillation column (3), the product mixture is then separated. The low boiler, preferably the ester formed in the transesterification, is removed via the top. The distillation column is preferably operated such that the water added upstream of the fixed bed reactor is likewise removed as the top product. The vaporous stream drawn off at the top is condensed in a condenser (12) and then separated in a decanter (13) into the aqueous phase and product ester-containing phase. The aqueous phase can be discharged to the workup via the line (15) or returned fully or partly back into the reaction via line (17). The stream of the ester-containing phase can be conducted via line (14) partly as reflux (16) to the column or discharged partly from the still. The high boiler, preferably the acid formed in the cross-transesterification, is discharged from the column (19) as a bottom stream.

The α-hydroxycarboxylic acid obtained from the reaction, for example hydroisobutyric acid, can be dehydrated in a known manner in a further step E). In general, the α-hydroxycarboxylic acid, for example the α-hydroxyisobutyric acid, is heated in the presence of at least one metal salt, for example of alkali metal and/or alkaline earth metal salts, to temperatures in the range from 160-300° C., more preferably in the range from 200 to 240° C., generally to obtain the (meth)acrylic acid and water. The suitable metal salts include sodium hydroxide, potassium hydroxide, calcium hydroxide, barium hydroxide, magnesium hydroxide, sodium sulphite, sodium carbonate, potassium carbonate, strontium carbonate, magnesium carbonate, sodium bicarbonate, sodium acetate, potassium acetate and sodium dihydrogenphosphate.

The dehydration of the α-hydroxycarboxylic acid can be performed preferably at a pressure in the range from 0.05 bar to 2.5 bar, more preferably in the range from 0.1 bar to 1 bar.

The dehydration of α-hydroxycarboxylic acids is described, for example, in DE-A-176 82 53.

The (meth)acrylic acid thus obtained can in turn be used to prepare alkyl (meth)acrylates. In addition, (meth)acrylic acid is a commercial product. Surprisingly, the process for preparing alkyl (meth)acrylates can accordingly likewise serve to prepare (meth)acrylic acid, in which case the product ratio of alkyl (meth)acrylates to (meth)acrylic acid can be regulated easily by the concentration of water in the transesterification of the alkyl α-hydroxycarboxylate and/or by the reaction temperature.

The process according to the invention can be considered as a component step of a process for preparing polymers or for producing moulding materials and polymer mouldings, and so these processes which are performed using the present invention are likewise novel and inventive.

The (meth)acrylates obtainable in accordance with the invention, especially methyl methacrylate which is to be prepared with preference, can be converted to polymers by free-radical means.

These polymers are generally obtained by free-radical polymerization of mixtures which comprise methyl methacrylate. In general, these mixtures contain at least 40% by weight, preferably at least 60% by weight and more preferably at least 80% by weight, based on the weight of the monomers, of methyl methacrylate.

In addition, these mixtures may comprise further (meth)acrylates copolymerizable with methyl methacrylate. The expression "(meth)acrylates" embraces methacrylates and acrylates and mixtures of the two.

These monomers are widely known. They include (meth)acrylates which derive from saturated alcohols, for example methyl acrylate, ethyl (meth)acrylate, propyl (meth)acrylate, n-butyl (meth)acrylate, tert-butyl (meth)acrylate, pentyl (meth)acrylate and 2-ethylhexyl (meth)acrylate;

(meth)acrylates which derive from unsaturated alcohols, for example oleyl (meth)acrylate, 2-propynyl (meth)acrylate, allyl (meth)acrylate, vinyl (meth)acrylate; aryl (meth)acrylates such as benzyl (meth)acrylate or phenyl (meth)acrylate, where the aryl radicals may each be unsubstituted or up to tetrasubstituted;

cycloalkyl (meth)acrylates such as 3-vinylcyclohexyl (meth)acrylate, bornyl (meth)acrylate;

hydroxyalkyl (meth)acrylates such as
3-hydroxypropyl (meth)acrylate,
3,4-dihydroxybutyl (meth)acrylate,
2-hydroxyethyl (meth)acrylate, 2-hydroxypropyl (meth)acrylate;

glycol di(meth)acrylates such as 1,4-butanediol (meth)acrylate, (meth)acrylates of ether alcohols, such as
tetrahydrofurfuryl (meth)acrylate, vinyloxyethoxyethyl (meth)acrylate;

amides and nitriles of (meth)acrylic acid, such as
N-(3-dimethylaminopropyl)(meth)acrylamide,
N-(diethylphosphono)(meth)acrylamide,
1-methacryloylamido-2-methyl-2-propanol;
sulphur-containing methacrylates such as
ethylsulphinylethyl (meth)acrylate,
4-thiocyanatobutyl (meth)acrylate,
ethylsulphonylethyl (meth)acrylate,
thiocyanatomethyl (meth)acrylate,
methylsulphinylmethyl (meth)acrylate, bis((meth)acryloyloxyethyl) sulphide;
polyfunctional (meth)acrylates such as
trimethylolpropane tri(meth)acrylate.

In addition to the (meth)acrylates detailed above, the compositions to be polymerized may also comprise further unsaturated monomers which are copolymerizable with methyl methacrylate and the aforementioned (meth)acrylates.

These include 1-alkenes such as hexene-1, heptene-1; branched alkenes, for example vinylcyclohexane, 3,3-dimethyl-1-propene, 3-methyl-1-diisobutylene, 4-methylpentene-1; acrylonitrile; vinyl esters such as vinyl acetate;
styrene, substituted styrenes with an alkyl substituent in the side chain, for example α-methylstyrene and α-ethylstyrene, substituted styrenes with an alkyl substituent on the ring, such as vinyltoluene and p-methylstyrene, halogenated styrenes, for example monochlorostyrenes, dichlorostyrenes, tribromostyrenes and tetrabromostyrenes; heterocyclic vinyl compounds such as 2-vinylpyridine, 3-vinylpyridine, 2-methyl-5-vinylpyridine, 3-ethyl-4-vinylpyridine, 2,3-dimethyl-5-vinylpyridine, vinylpyrimidine, vinylpiperidine, 9-vinylcarbazole, 3-vinylcarbazole, 4-vinylcarbazole, 1-vinylimidazole, 2-methyl-1-vinylimidazole, N-vinylpyrrolidone, 2-vinylpyrrolidone, N-vinylpyrrolidine, 3-vinylpyrrolidine, N-vinylcaprolactam, N-vinylbutyrolactam, vinyloxolane, vinylfuran, vinylthiophene, vinylthiolane, vinylthiazoles and hydrogenated vinylthiazoles, vinyloxazoles and hydrogenated vinyloxazoles;
vinyl and isoprenyl ethers;
maleic acid derivatives, for example maleic anhydride, methylmaleic anhydride, maleimide, methylmaleimide; and dienes, for example divinylbenzene.

In general, these comonomers are used in an amount of 0% by weight to 60% by weight, preferably 0% by weight to 40% by weight and more preferably 0% by weight to 20% by weight, based on the weight of the monomers, the compounds being useable individually or as a mixture.

The polymerization is generally initiated with known free-radical initiators. The preferred initiators include the azo initiators widely known in the technical field, such as AIBN and 1,1-azobiscyclohexanecarbonitrile, and peroxy compounds such as methyl ethyl ketone peroxide, acetylacetone peroxide, dilauryl peroxide, tert-butyl per-2-ethylhexanoate, ketone peroxide, methyl isobutyl ketone peroxide, cyclohexanone peroxide, dibenzoyl peroxide, tert-butyl peroxybenzoate, tert-butyl peroxyisopropylcarbonate, 2,5-bis(2-ethylhexanoylperoxy)-2,5-dimethylhexane, tert-butyl peroxy-2-ethylhexanoate, tert-butyl peroxy-3,5,5-trimethylhexanoate, dicumyl peroxide, 1,1-bis(tert-butyl-peroxy)cyclohexane, 1,1-bis(tert-butylperoxy)-3,3,5-trimethylcyclohexane, cumene hydroperoxide, tert-butyl hydroperoxide, bis(4-tert-butylcyclohexyl)peroxydicarbonate, mixtures of two or more of the aforementioned compounds with one another and mixtures of the aforementioned compounds with unspecified compounds which can likewise form free radicals.

These compounds are frequently used in an amount of 0.01% by weight to 10% by weight, preferably of 0.5% by weight to 3% by weight, based on the weight of the monomers.

The polymerization can preferably be performed at a temperature in the range from 20° C. to 120° C.

The preparation of the (meth)acrylate homo- and/or copolymers from (meth)acrylates by the various methods of free-radical polymerization is known per se. For instance, the polymers can be prepared in bulk, solution, suspension or emulsion polymerization. Bulk polymerization is described, by way of example, in Houben-Weyl, Volume E20, part 2 (1987), p. 1145ff. Valuable information regarding solution polymerization can be found in that same publication at p. 1156ff. Details of the suspension polymerization technique can be found in that same publication at p. 1149ff., while emulsion polymerization is detailed and explained in that same publication at p. 1150ff.

The polymers detailed above can especially be used to produce moulding materials which may typically comprise, as well as the polymers, additives, for example colorants, pigments, for example metallic pigments, UV stabilizers or fillers. The proportion of these additives depends on the intended application and may therefore be within a wide range. This proportion, if additives are present, may preferably be 0 to 30% by weight, more preferably 0.1 to 5% by weight.

The preferred moulding materials and polymers can be processed to mouldings by means of customary moulding methods, for example injection moulding or extrusion, and the present invention likewise provides processes for producing mouldings, said processes being performed using polymers which have been obtained by a process according to the invention.

In addition, the alkyl (meth)acrylates, especially methyl methacrylate, which have been obtained by means of a process according to the invention can be used to produce cast glass. These polymers obtained by the casting chamber method have a particularly high molecular weight and therefore exhibit different mechanical properties from the thermoplastically processable polymers. The present invention likewise provides processes for producing these mouldings, said processes being performed using (meth)acrylates which have been obtained according to the present process.

The present invention will be illustrated in detail hereinafter with reference to an example.

EXAMPLE 1

A mixture comprising 1 mol of HCN, 2.5 mol of acetone and 200 ppm of $Li_2O$ was prepared and converted at 20° C. until equilibrium was established. The resulting reaction mixture comprised 47.7% by weight of acetone cyanohydrin and 51.5% by weight of acetone. The HCN content was less than 8000 ppm.

A mixture of this composition was transferred continuously to a hydrolysis reactor, in which 38.6% by weight of water were added. In the course of this, the HCN content remained essentially unchanged.

The water was added partly from a reflux, which was obtained from the bottom in a purification of the reaction mixture after the hydrolysis of the acetone cyanohydrin. The hydrolysis was performed using an $MnO_2$ catalyst, which is explained in detail especially in the examples of WO 2008/061822. Air was used to stabilize the catalyst, as described in Example 1 of the publication WO 2008/061822. The pH was 9.0.

The carboxamide was removed via the bottom in a first distillation step from the reaction mixture obtained after the hydrolysis, and this distillation was performed at a temperature of 175° C. (bottom temperature) and a pressure of 0.4 bar.

The top product comprising 52% by weight of water, 43% by weight of acetone, 4.8% by weight of acetone cyanohydrin and 0.2% by weight of HCN was purified continuously by means of a distillation column with internals, by adding a stream of 1.2 kg/h. 0.3 kg of acetone was supplied via the reflux of the column, so as to achieve a high separating performance. The distillation system had an unlimited service life, i.e. no decrease in the separating performance was found in 60 days. No HCN could be detected in the bottom product. The top product comprised 86% by weight of acetone, 5.8% by weight of acetone cyanohydrin, 0.2% by weight of HCN and 8% by weight of water.

The service life of the catalyst was more than 60 days, the service life of the catalyst being defined as the time until the level of conversion falls below 50% of the starting level of conversion.

The invention claimed is:

1. A process for preparing a carboxamide from a carbonyl compound and hydrogen cyanide, comprising:
   A) reacting a carbonyl compound with hydrogen cyanide to prepare a hydroxycarbonitrile in a first reaction mixture;
   B) hydrolyzing the hydroxycarbonitrile obtained in A) in the presence of an ionizable lithium compound and a catalyst comprising manganese dioxide to prepare a second reaction mixture,
   wherein a molar excess of carbonyl compound in relation to the hydrogen cyanide is present in the reacting A),
   wherein the first reaction mixture obtained in A) is not purified by distillation before the hydrolyzing B) is performed,
   wherein the second reaction mixture obtained after B) is purified by a two-stage distillation wherein a resulting carboxamide and water are separated from a third mixture which comprises a recovered carbonyl compound and at least one selected from the group consisting of the hydroxycarbonitrile and the hydrogen cyanide, and the water is separated from the resulting carboxamide in a further distillation,
   wherein a composition which comprises the carbonyl compound reacted in A) is introduced via a reflux into a still employed to separate the water and the hydrogen cyanide,
   wherein the composition introduced into the reflux has a lower proportion of HCN than a second composition withdrawn via the top of the still.

2. The process of claim 1, wherein a molar ratio of the carbonyl compound to the hydrogen cyanide is in a range from 1.1:1 to 7:1.

3. The process of claim 2, wherein a molar ratio of the carbonyl compound to the hydrogen cyanide is in a range from 1.5:1 to 5:1.

4. The process of claim 1, wherein the resulting carboxamide is separated from the water in a multistage evaporative concentration.

5. The process of claim 1, wherein an amount of the carbonyl compound added is sufficient to prepare an amount of hydroxycarbonitrile envisaged in A).

6. The process of claim 1, wherein the recovered carbonyl compound obtained by the two-stage distillation is employed to prepare the hydroxycarbonitrile in A).

7. The process of claim 1, wherein the carbonyl compound in A) is acetone.

8. The process of claim 1, wherein the reacting A) is performed at a temperature in a range from −10 to 50° C.

9. The process of claim 1, wherein the reacting A) is performed at a pressure in a range from 0.3 bar to 3 bar.

10. The process of claim 1, wherein molar ratio of water to the hydroxycarbonitrile in the hydrolyzing B) is in a range of 0.5:1-25:1.

11. The process of claim 1, wherein the hydrolyzing B) is performed at a temperature in a range from 10 to 150° C.

12. The process of claim 1, wherein the hydrolyzing B) is performed at a pressure in a range from 0.1 bar to 10 bar.

13. A process for preparing at least one alkyl(meth)acrylate, comprising:
   performing the process of claim 1; and
   processing further in order to prepare the at least one alkyl (meth)acrylate.

14. The process of claim 13, wherein the at least one alkyl(meth)acrylate comprises methyl methacrylate.

15. The process of claim 1, wherein the lithium compound is a water-soluble lithium salt.

16. The process of claim 1, wherein the lithium compound is present in a concentration range of 0.001 to 5% by weight.

17. The process of claim 16, wherein the concentration range is 0.01 to 1% by weight.

* * * * *